United States Patent
Cole et al.

(10) Patent No.: US 11,504,069 B2
(45) Date of Patent: *Nov. 22, 2022

(54) METHOD AND APPARATUS TO INFER OBJECT AND AGENT PROPERTIES, ACTIVITY CAPACITIES, BEHAVIORS, AND INTENTS FROM CONTACT AND PRESSURE IMAGES

(71) Applicants: Michael John Cole, New York, NY (US); Gerald Seidman, New York, NY (US)

(72) Inventors: Michael John Cole, New York, NY (US); Gerald Seidman, New York, NY (US)

(73) Assignee: Tactonic Technologies, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/455,194

(22) Filed: Jun. 27, 2019

(65) Prior Publication Data

US 2019/0313978 A1 Oct. 17, 2019

Related U.S. Application Data

(63) Continuation of application No. 14/661,826, filed on Mar. 18, 2015, now Pat. No. 10,335,091.

(Continued)

(51) Int. Cl.
*A61B 5/00* (2006.01)
*G01L 5/16* (2020.01)
(Continued)

(52) U.S. Cl.
CPC .......... *A61B 5/7267* (2013.01); *A61B 5/1038* (2013.01); *A61B 5/112* (2013.01);
(Continued)

(58) Field of Classification Search
CPC . G06F 2203/04103; G06F 2203/04112; G06F 2203/04113; G06F 3/005; G06F 3/0414; G06F 3/044; G06F 3/045; G06F 2203/04101; G06F 2203/04104; G06F 2203/04105; G06F 2203/04106;
(Continued)

(56) References Cited

U.S. PATENT DOCUMENTS 5,952,585 A * 9/1999 Trantzas .............. A61B 5/1038
73/862.046
8,494,222 B2 * 7/2013 Cobb ................. G06K 9/00771
382/103

(Continued)

*Primary Examiner* — Robert G Bachner
(74) *Attorney, Agent, or Firm* — Ansel M. Schwartz

(57) ABSTRACT

An apparatus for determining a non-apparent attribute of an object having a sensor portion with which the object makes contact and to which the object applies pressure. The apparatus has a computer in communication with the sensor portion that receives signals from the sensor portion corresponding to the contact and pressure applied to the sensor portion, and determines from the signals the non-apparent attribute. The apparatus has an output in communication with the computer that identifies the non-apparent attribute determined by the computer. A method for determining a non-apparent attribute of an object.

3 Claims, 11 Drawing Sheets

Related U.S. Application Data

(60) Provisional application No. 61/955,406, filed on Mar. 19, 2014.

(51) Int. Cl.
*A61B 5/103* (2006.01)
*A61B 5/11* (2006.01)
*G06V 40/10* (2022.01)
*G06V 40/20* (2022.01)

(52) U.S. Cl.
CPC .......... *A61B 5/1116* (2013.01); *A61B 5/1123* (2013.01); *A61B 5/4023* (2013.01); *A61B 5/4088* (2013.01); *A61B 5/6892* (2013.01); *G01L 5/16* (2013.01); *G06V 40/10* (2022.01); *G06V 40/25* (2022.01); *A61B 5/7246* (2013.01)

(58) Field of Classification Search
CPC ...... G06F 3/011; G06F 3/0304; G06F 3/0416; G06F 3/047
See application file for complete search history.

(56) References Cited

U.S. PATENT DOCUMENTS

| | | |
|---|---|---|
| 10,335,091 B2 * | 7/2019 | Cole |
| 2010/0035727 A1 * | 2/2010 | Brunner ............... A61B 5/1038 482/8 |
| 2012/0086659 A1 * | 4/2012 | Perlin ..................... G06F 3/011 345/173 |

* cited by examiner

METHOD AND APPARATUS TO INFER OBJECT AND AGENT PROPERTIES, ACTIVITY CAPACITIES, BEHAVIORS, AND INTENTS FROM CONTACT AND PRESSURE IMAGES

CROSS-REFERENCE TO RELATED APPLICATIONS

This is a continuation of U.S. patent application Ser. No. 14/661,826 filed Mar. 18, 2015, now U.S. Pat. No. 10,335,091, which is a nonprovisional of U.S. provisional application Ser. No. 61/955,406 filed on Mar. 19, 2014, all of which are incorporated by reference herein.

FIELD OF THE INVENTION

The invention involves techniques and a system to acquire and analyze pressure contact patterns. (As used herein, references to the "present invention" or "invention" relate to exemplary embodiments and not necessarily to every embodiment encompassed by the appended claims.) More specifically, the invention provides a system that is able to learn properties of objects and their behaviors by analyzing data about the points of object contact with a surface. Aspects of the invention utilize pressure data from the forces the objects impart on a pressure sensing surface. The analysis of the data involves one or more layers of classification and sequencing. The objects can be inanimate, including but not limited to immobile objects and cars, trucks, and forklifts, or humans or other agents, such as robots, remotely controlled vehicles, etc. Inferred object properties, behaviors, and/or intents can be associated with objects and permit the system to perform various useful and beneficial actions. The system is able to determine certain object states, including but not limited to detecting when a person is walking or when they are in an awkward pose. The invention enables automated detection and tracking of path and activity, and inference of behaviors and other states of the agent based on the path and features of their respective pressure patterns. This system is able to learn, over time through the use of what are generally referred to as machine learning algorithms, to identify additional behaviors at progressively more complex levels of abstraction. Human or agent intent can be learned from the identification of certain behaviors and sequences of behaviors including but not limited to historically gathered and/or generated results.

One useful aspect of the invention relates to automatic measurement of the properties of a person's gait, balance, general activity, and other features extracted from the pressure images resulting from the person's interaction with pressure measuring sensors on or under the floor and use of those measurements to predict certain physical capacities of the person at the time of interaction or at a future date. The invention provides a means to monitor changes in gait parameters, physical capacities, and activity over time and to report those changes to a user or system locally or in a remote location. The invention provides an automated and objective procedure that can be substituted for human judgments of a person's capacity to maintain balance and their risk of falling. Predictions of diminished physical capacities are used to predict the propensity to fall, and changes in gait parameters can monitor the progression of certain diseases. The measurements of gait, balance, and activity can be used to monitor the person's ergonomic performance and provide a means to give feedback information to the worker or to a system in order to reduce risk or increase the overall performance and efficiency of the work and the system.

Another useful aspect of the invention relates to identifying properties of objects, people and agents on a surface and tracking them over time. These properties and the locomotion paths are used to infer various activities and behaviors of the objects, including but not limited the attribution of mental or affective states and intentions. These inferences are useful, for example in settings of general activity monitoring, security systems, and commercial retailing. The invention can provide information to other systems or act on the information to monitor, make a decision, or take an action. For example, the system might make a commercial offer to a person or group of people who are shopping, or it might flag the activity of a person or object as unusual, suspicious, or potentially nefarious.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

The problem of detection of a human or agent's properties, behaviors, and intents has a long history. Much of the work has involved the acquisition of data by non-contact means. Most commonly, visual images have been acquired from various types of cameras and those images have been processed to infer salient information. While most non-contact data acquisition has been in the visible or near-visible part of the spectrum, other non-contact techniques to acquire observations have been used, including ones based on acoustic and infrared ranging sensing.

Use of data from direct contact with a sensing surface has also been exploited. These include occlusion systems, where the object is sensed because it blocks electromagnetic radiation in parts of the spectrum. There has also been prior work on extracting features from floor surface image data, including identification of objects (U.S. Pat. No. 8,138,882), imaging of footsteps and parts of people, and from local surface pressure measurements to characterize gait (U.S. Pat. No. 5,952,585), and to identify people. There does also exist work on tracking people using floor-sensed data.

This direct contact sensing work has used several sensing techniques. Branzel et al. (2013) describe a system that uses a camera mounted beneath a floor to image the contact of people and other objects with the floor. The system processes the visual images of the pressure contact of the objects rather than measurements of the pressure imparted by the object. Connected component analysis is applied to the image pixels to identify and track continuous areas of contact. Image features, such as image moments and shape descriptors were calculated and used as inputs to a trained feed forward neural network to assign a probability the image area matched one of seven object labels, e.g. hand, shoe, previously stored in a database. A set of heuristic association rules are used to identify particular location configurations of identified pressure image parts as being one of five poses: standing, kneeling, sitting on the floor, sitting on cube seat or sofa, and lying on a sofa.

Person tracking with floor-sensed data from pressure-activated switches or capacitive sensors Bibliography entry uses only the successive activation of the on-off pressure sensors for tracking by sensing contact. These systems do use other features of a person's locomotion, including gait parameters, or distinguish features of the path, such as turning characteristics, or actions along the path. Pressure is not sensed directly, although certain events, such as something striking the surface can be inferred.

Bibliography entry shows how sensed movement trajectories using a capacitive sensing system can be combined with heuristic rules to distinguish 'normal' behavior from unusual trajectories. For example, footsteps that begin at a window entrance may be indicative of a break-in in a home with a floor sensing system.

U.S. Pat. No. 8,138,882 discloses a system to identify an object on a floor by matching the detected contact shape with a shape profile stored in a database and then performing an action if some threshold values are exceeded. It describes applications in securing a premises, for example, detecting whether a person is authorized to be in a location, or that a child has entered the premises. The system can then take some action, for example, to alter lighting or notify the police or a caregiver.

U.S. Pat. No. 5,952,585 discloses a pressure sensing array apparatus that uses a plurality of current driven electrode pressure sensors to measure properties of footsteps and gait. Commercial versions, e.g. the Gaitrite system by CIR Systems, are used by clinicians to measure the gait parameters of a single person in a defined protocol of walking to support physical therapy after injuries, make analysis of gait to improve athletic performance, and to monitor the progression of certain diseases.

Although there has been work using surface contact images and pressure data to identify objects, parts of people, animals and agents, it is valuable to be able to infer specifically the classification, actions, behaviors, intents, and other properties of humans and agents in a general way and automatically. In the case of humans, such other properties include age range, gender, whether or not they have some level of knowledge, whether they are in a state of making a decision, whether they are searching for an object or information, whether they are having difficulty performing a task, and so on. Previous work on use of contact images and localized pressure data has focused only on the extraction of physical properties and their association with features in the pressure profile, or over time, for example in tracking physical location. This invention relates to extracting both physical properties of objects and associating mental and other states and properties of a human or agent, including classifications such as activity states, gender, and age, which are not immediately discernible in the pressure image and collections of pressure images.

Gait and footsteps have been studied to extract behavioral biometrics Bibliography entry. Gait has usually been studied via visual recognition systems and investigated for use in fields such as surveillance, medical applications, design and selection of sports shoes, and analysis of athletic motions and performance.

One specific and valuable problem is to measure the changing physical and mental capacities of the elderly. Heretofore, this has been performed mostly by expert human judgment based on interviewing the person, making physical measurements, and assessing the results of standard physical or mental performance tests. Such assessments can be used to assist the person to anticipate deteriorating abilities, adjust activities, and otherwise ameliorate the person's situation.

An acute problem is the prediction of a propensity to fall. Falls amongst the elderly are a significant cause of morbidity and mortality. Age-related reduction of physical capacities expressed in postural balance and gait function have been consistently linked with falls. Therefore, various laboratory and clinical tests of balance and gait have been used in attempts to predict the risk of falling.

Current practice is for a professional to conduct several tests of the person's balance and gait in a controlled setting, usually a doctor's office or clinic. Typical tests include timing the patient to rise from a seated position and begin walking (TUG test), and making gait measurements using systems, such as one available from Zenometrics LLC. Using this data, the expert makes a judgment about the person's physical capacity and their propensity to fall. One problem is that these judgments are somewhat subjective and experts may vary in their judgment given the same data and/or observations. Further, because the testing procedure takes place in a clinical setting, there are significant impediments to monitoring a patient as their physical capacities decline with age. These include cost of each visit and test, the availability of experts, and the continuity, availability, and consistency of records over time. Further, there are benefits to making gait observations during a person's natural activities because research shows that gait parameters measured in clinical settings are significantly different than those measured when a person is outside the clinical setting Bibliography entry. In addition, there is benefit to frequent observations of a person's gait.

It is desirable to have an automated procedure that predicts the propensity to fall because it can be used constantly and because it can be used by non-experts, including the elderly person and those with the responsibility of care giving. Another important benefit of an automated procedure is its ability to facilitate objective decision-making about future risks that can result in more optimal cost-benefit choices about the elderly person's living situation, for example, whether continued independent living is significantly more risky than before.

The problem of making an objective automated solution requires a means to automatically collect the observations and providing a computable representation that can be used to produce automatic objective judgments of the risk of falling that correlate well with human-based assessments. To achieve broad application of the solution in non-clinical settings it is desirable to be able to collect observations and analyze normal walking activities.

Gait characteristics have been correlated with human cognitive capacities and states, both in terms of current activities and future capacities. Certain pathological conditions are believed to affect brain function in ways that affect gait, for example by impacting motor control or split attention capacities Bibliography entry. Gait analysis and physiological tests such as rising from a seated position and beginning to walk (TUG test) can also be used to detect and predict cognitive declines of an individual. Greene describes such a system in EP2688006 A2 where inertial sensors attached to a person are used to detect gait characteristics and the inertial data can be used by a classifier to predict the future cognitive capacity of the person based on changes in the inertial data compared to a baseline.

One cause of work-related musculoskeletal disorder injuries for assembly line workers is repetitive actions where the worker assumes an awkward pose. Such injuries are estimated to cost many billions of dollars annually in compensation costs, lost wages, and lost production. The automotive industry has been a leader in this area because of significant costs due to injuries, legal action by unions, state worker compensation boards, and the insurance industry. Recognized benefits of good ergonomic design include increased factory efficiency and product quality.

Pressure patterns have been used to identify people Bibliography entry using the trajectory of the center of pressure in gait and pressure patterns of the individual footsteps. While high identification rates can be achieved in controlled settings, it is desirable to improve identification rates. Additional independent features from pressure measurements at different time scales, for example, gait parameters and locomotion behaviors, can improve classification and identification rates and reduce false positives.

Locomotion is under cognitive control and velocity patterns allow inference of locomotion goals, for example people orient themselves in ways that reflect their visual attention Bibliography entry. Visual data has been analyzed and used to automatically classify individual activity and behavior, for example as shown by Bibliography entry, to automatically identify anomalous behavior, for example as disclosed in U.S. Pat. No. 8,494,222, and to identify social relationships between people, for example as disclosed in U.S. Pat. No. 7,953,690.

Visual image-based systems have various challenges and limitations, including acquisition and simultaneous tracking of multiple objects at differing distances and with changing scale. Objects can be partially or fully-occluded and salient visual features may be cloaked. These types of limitations contribute to uncertainty in recognition and identification of objects and their properties, as well as to uncertainties in any further analysis of the data or taking action based on the data. Such uncertainties and other difficulties limit the utility of such systems in many settings, including automated security applications. They also make it difficult to extend such systems to provide new types of utility, for example attribution of behaviors to people that can be interpreted in specific contexts, such as retail shopping activity and intent. Useful object properties such as weight and detailed gait and locomotion parameters are hard to extract in uncontrolled settings. Visual systems also tend to have demanding processing requirements for large scale multi-object settings because of the need to process the images to perform basic object recognition and discern other structure in the image.

The invention makes classifications of objects and inferences about the properties and behaviors of objects based on direct measurement of the object's contact with a surface. In this way the invention solves many of the challenges and limitations of applying established methodologies and inference techniques to visual data in order to make object classifications and inferences with higher quality and better system performance.

OBJECTS OF THE INVENTION

It is an object of this invention to provide a means to automatically collect contact and/or pressure measurements of contact and locomotion of one or more objects on a surface.

Another object of this invention is to collect such measurements over time and make calculations on those measurements, especially changes in the values.

Another object of the invention is to infer properties of an object or agent that are not directly observable in contact or pressure measurements, for example as general classification of the object or a human in groupings of age, mental or physical capacity, or gender, agent actions or behaviors or intents, etc.

Another object of the invention is to track objects including humans and agents on a surface.

Another object of the invention is to differentiate and/or identify people moving on a surface.

Another object of this invention is to provide a means to record and monitor the path of an object or agent from patterns of contact and/or pressure on a floor surface.

Yet another object of the invention is to measure aspects of gait, the gait velocity and balance of a person while they are standing, walking or otherwise moving.

Another object of the invention is to calculate the future risk of falling from measurements and/or repeated measurements of the gait velocity and balance of a person.

Another object of the invention is to calculate the future cognitive capacity from measurements and/or repeated measurements of the gait velocity and balance of a person.

Yet another object of the invention is to identify patterns of the changes in measurements and to calculate the correlation of those patterns with changes in patterns of expert judgments about the future risk of falling from a reference collection.

Yet another object of the invention is to identify patterns of the changes in measurements and to calculate the correlation of those patterns with changes in patterns of expert judgments about the future cognitive capacity from a reference collection.

Another object of this invention is to provide a means to infer the agent activity state and activity sequences from patterns of contact and/or pressure on a floor surface.

Another object is to record worker actions in a work environment, including detection of awkward poses, to support an ergonomic evaluation of the worker's activity in the work environment.

Another object is to measure the ergonomic parameters of a worker's activity to provide feedback to the worker and/or a system to modify the environment to improve the worker's ergonomic situation.

Another object of the invention is to provide a means to attribute behaviors to one or more objects, both individually and collectively.

Another object of the invention is to provide a means to infer social and other relationships between an agent and one or more other agents.

Another object of the invention is to provide a means to attribute intention to an agent based on patterns of contact and/or pressure on a floor surface.

Yet another object of the invention is to use inferences from various of the invention objects as evidence for systems that communicate or signal the agent for some purpose, for example by making a commercial offer, providing information, making a warning, or changing some aspect of the environment, such as lighting.

Yet another object of the invention is to use inferences from various of the invention objects as evidence for systems that make decisions about the agent for some purpose, for example by classifying the agent or the agent's activities or behavior.

Yet another object of the invention is to provide a means to provide information to another system about the properties, actions, behaviors or intents of the agent(s), for example by tracking, classifying or identifying the agent(s) or their actions, behaviors and/or intents. A specific example is identifying unusual or threatening behavior.

An additional object of the invention is to provide a technique for inferring mental and/or internal states of an agent without requiring a priori knowledge of the agent properties, the tasks in which the agent is engaged, or of the agent's intentions, or the contents or locations of specific regions that situate the agent.

Another object of the invention is to simultaneously perform one or more of the above invention objects for multiple humans and/or agents on a unified or distributed contact or pressure sensing surface.

Still other objects and advantages of the invention will in part be obvious and will in part be apparent from the specification and drawings.

The utility and advantages of the ability to accomplish the above invention objects includes the ability to automate such inferences and predictions and take appropriate action, including to assist, inform, or otherwise interact with the object or agent. Examples include automatic user interface changes, adjustment of machinery, tools or other tangible objects in order to better accomplish a task, identification of a context for the agent in order to decide to provide appropriate information, engage in a dialog, making an offer, etc. Another general benefit of achieving one or more of the invention objects is to use the information about the agent and the agent's context in other systems, for example aggregating audiences for a product brand, which is of significant value to advertisers, or using the information to make individual models of the user or general user models that are valuable in other contexts, for example to provide support, etc. in future tasks, such as information search or emergency intervention.

BRIEF SUMMARY OF THE INVENTION

These objects and advantages are provided by a computer-implemented method for inferring but not limited to the following: physical, behavioral, mental and internal states of an agent, and other properties of an object or agent, from measurements of contact or pressure imparted by the agent onto a pressure-sensing surface. The method includes identifying contact points and/or elementary features of the spatio-temporal pressure data, such as contact positions and force, and changes thereof.

The use of measurements of contact and pressure provide direct measurements of objects allow the invention to overcome many limitations and practical implementation problems that arise because of the challenges of processing remotely sensed data in image-based systems. Many representation, recognition and inference techniques used for visual data can be applied to contact and pressure data with suitable adjustments that will be apparent to those practiced in the art of data analysis and machine learning. Usable representations of an object can be fashioned from contact and/or pressure measurements using far fewer data samples than are required to process visual images. This permits the invention to better overcome certain data processing and storage challenges that can arise in multi-object settings and for analysis of data from large areas and for situations where the analysis resource overhead needs to be minimized, for example to provide fast analysis and output to an application that acts on the analysis result.

Sensing apparatuses that can make inertial measurements of movement and activity attached directly to the objects have practical limitations when it is desirable to learn properties of objects on a surface in an unobtrusive manner and over extended periods of time. The use of measurements of contact and pressure gathered from surface contact has advantages. All of the objects on a surface generate contact and pressure data, not just those specially instrumented, and the measurements have a uniform scale with no special calibration or validation required to enable comparison between object contact and pressure properties or for derived features and properties. These advantages are apparent and confer utility for sensed surfaces in uncontrolled environments, and when a plurality of objects need to be processed, and when the data is collected or compared over extended periods of time.

In order to automatically collect data about locomotion across a surface a contact and/or pressure sensing system is used. In the preferred embodiment, it employs a plurality of arrayed pressure sensing elements for example by using a mechanically interpolating pressure sensing system such as Tactonic Technology LLC's pressure sensing floor tiles. The system provides direct measurement of the contact and/or pressure imparted by an object on the floor for each unit of time.

In order to overcome the basic problem of inferring properties of objects, agents, and humans that are not immediately discernible from contact or pressure data, data is collected from a surface contact or pressure sensing system and that data is analyzed as a time series or in other ways. The analysis can be on-line or deferred for later processing. The analysis consists of a combination of signal processing and machine learning using the surface contact or pressure data, and various derivations thereof, Including but not limited to a time varying images of the applied pressures. The machine learning techniques include unsupervised, semi-supervised, and supervised methods known to those practiced in the art of mathematical modeling.

The collection of pressure data observations is processed to make numerical representations of the contact and/or pressure at the sensor points from digital or analog pressure values. The numerical representations are then processed using well-known clustering techniques, for example by using density-based clustering, to identify regions that have contact or pressure measurements of a distinct object, for example a human foot or a wheel. These measurements of the objects are then analyzed using statistical and other techniques known to those skilled in the art to make mathematical representations of the objects on the surface at a time and over time segments as appropriate to the desired result. Learned patterns of those representations can be classified using models derived from processing data for known examples of each class, or as a result of heuristic rules from human experience or association rules learned from data sets or learned Markov Logic Networks. Unsupervised techniques, such as but not limited to clustering and association rule mining, may also be used.

The data to process can be drawn from differing time scales or collection sampling as appropriate to the classification and predictive goal of the analysis and other requirements such as for on-line analysis or real-time prediction. For example, to measure human foot step properties, including balance, it is desirable to have a collection of moment to moment pressure measurements over the foot contact area. To measure gait parameters, such as velocity, it is desirable to have measurements of successive footsteps.

From pressure measurements and patterns of pressure measurements, properties of individual objects moving on a contiguous or distributed pressure surface can be measured and inferred. These properties can be direct physical properties of the object, such as its weight, velocity, and center of mass. Pressure measurements and pressure patterns over time provide a sufficient number of features to distinguish and identify objects, including people, using machine learning techniques including but not limited to clustering, decision trees, and other modeling techniques. Such techniques may be used alone or in combination with other modeling techniques to achieve useful prediction performance.

Use of statistical techniques to compare of patterns of gait and/or balance over time for an individual can indicate physical deterioration and can be projected to allow prediction of the probability of falling in some future time period.

The patterns of pressure measurements and derived object features in locomotion can be analyzed as a sequence of coherent path segments. These path segments can be classified using supervised, semi-supervised, or unsupervised machine learning techniques to infer the probable behavior of the agent. For example, an agent's pattern of path segments in a retail space, such as a mall, can distinguish different behaviors, for example browsing vs. shopping with a specific purchase goal. Further, such learned classification of changes in activity and locomotion states, for example orienting to a new direction and then slowing down or stopping, can be indicative of agent mental states, including information acquisition and decision making. Such observations of behaviors can be classified using models or by making similarity comparisons with stored behavior instances or general models of behaviors. Unusual or novel behaviors can be detected by setting appropriate similarity thresholds or applying heuristic or learned decision procedures. Analysis and association of the path segments of one agent with the path segments of other agents can indicate social or other relationships between agents, for example people working or shopping together. The confidence of such inferences can be improved with knowledge about location and other context features added to the input for modeling, for example the location of a store entrance or a departure gate in an airport terminal can aid human or automated rule-based interpretation of path-segment and activity sequence behaviors.

The invention accordingly comprises the several steps and the relation of one or more of such steps with respect to each of the others, and the apparatus embodying features of construction, combinations of elements and arrangement of parts that are adapted to affect such steps, all is exemplified in the following detailed disclosure, and the scope of the invention will be indicated in the claims.

The present invention pertains to an apparatus for determining a non-apparent attribute of an object. The apparatus comprises a sensor portion with which the object makes contact and to which the object applies pressure. The apparatus comprises a computer in communication with the sensor portion that receives signals from the sensor portion corresponding to the contact and pressure applied to the sensor portion, and determines from the signals the non-apparent attribute. The apparatus comprises an output in communication with the computer that identifies the non-apparent attribute determined by the computer.

The present invention pertains to a method for determining a non-apparent attribute of an object. The method comprises the steps of making contact and applying pressure with an object to a sensor portion. There is the step of receiving signals by a computer in communication with the sensor portion from the sensor portion corresponding to the contact and pressure applied to the sensor portion. There is the step of determining by the computer from the signals the non-apparent attribute. There is the step of identifying at an output in communication with the computer the non-apparent attribute determined by the computer.

The present invention pertains to a computer-implemented method to learn classifications and properties of one or more objects by processing a sequence of surface contact and/or pressure measurements captured by a plurality of local contact or pressure sensing system at a time and over time. The method comprises the steps of receiving a frame or frames of the sequence which includes data for a plurality of contact or pressure measurements included in the frame. There is the step of identifying one or more collections of contact and/or pressure measurements in the frame, where each collection represents an object on the surface. There is the step of generating models to extract one or more features from the contact and/or pressure measurement collections that are associated with each identified object. There is the step of extracting a plurality of features from the collections of contact and/or pressure measurements. There is the step of classifying each of the collections of contact and/or pressure measurements using a trained or untrained classifier. There is the step of supplying the extracted features and/or the object classifications from one or more frames to a machine learning engine. There is the step of using the machine learning engine to generate values for one or more properties of one or more objects and/or generate semantic representations of the behavior of one or more objects over a plurality of frames, where the machine learning engine is configured to learn properties and behavior patterns observed in the contact and/or surface pressure measurements over the plurality of frames and to identify patterns of behavior by the classified objects.

BRIEF DESCRIPTION OF THE SEVERAL VIEWS OF THE DRAWING

In the accompanying drawings, the preferred embodiment of the invention and preferred methods of practicing the invention are illustrated in which.

DETAILED DESCRIPTION OF THE INVENTION

Figure 2:
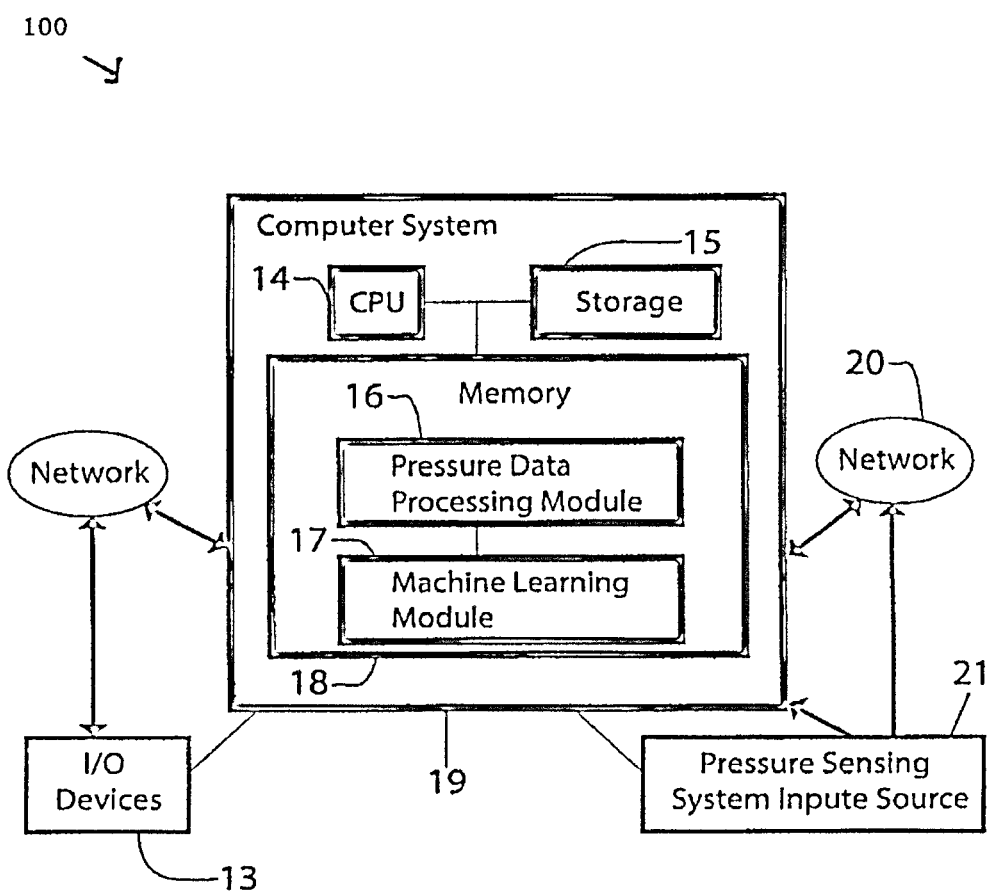
FIG. 2 shows a relationship of a machine learning module to the computer system.
Figure 5:
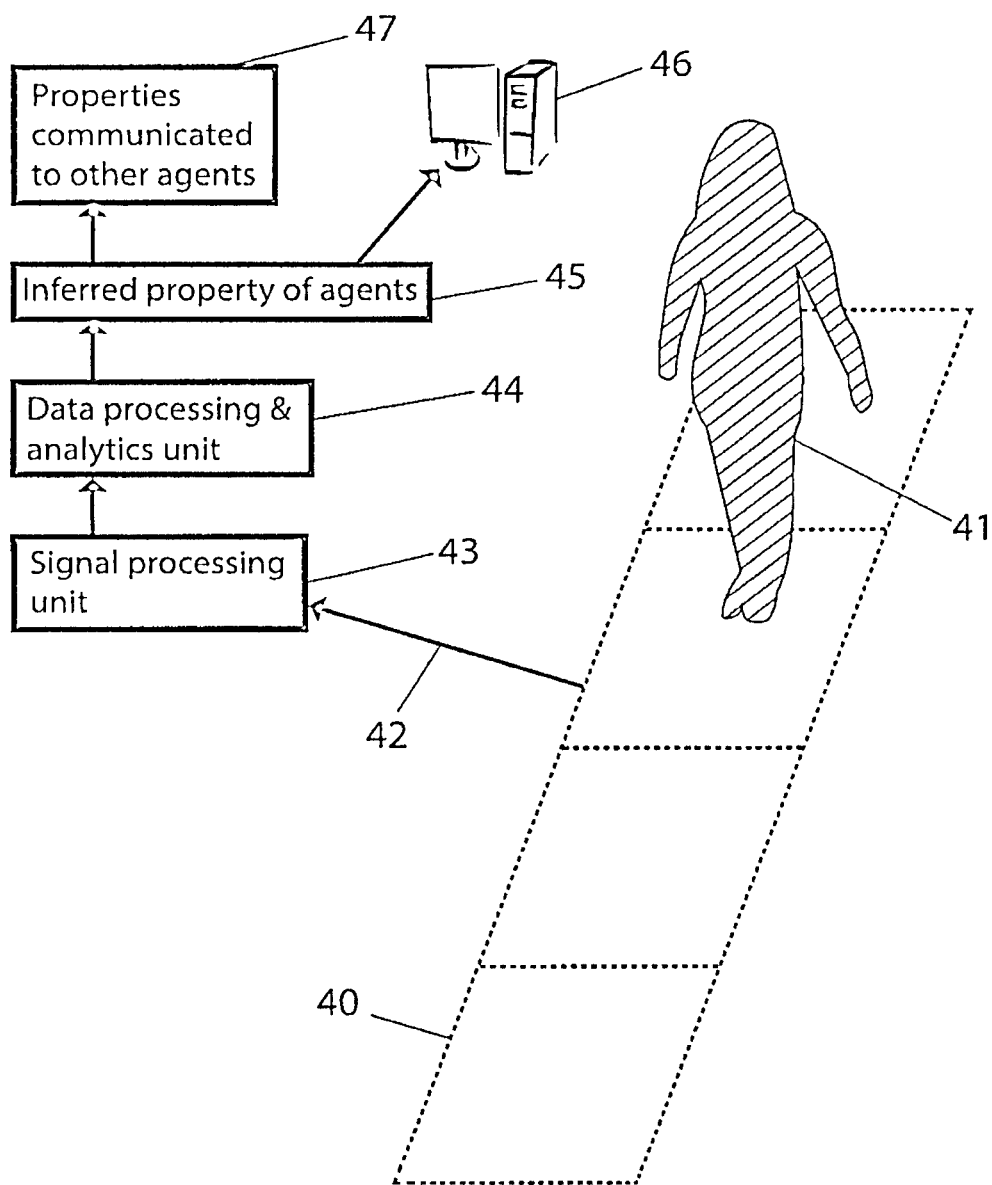
FIG. 5 shows a specific system to infer the risk of falling.
Figure 6:
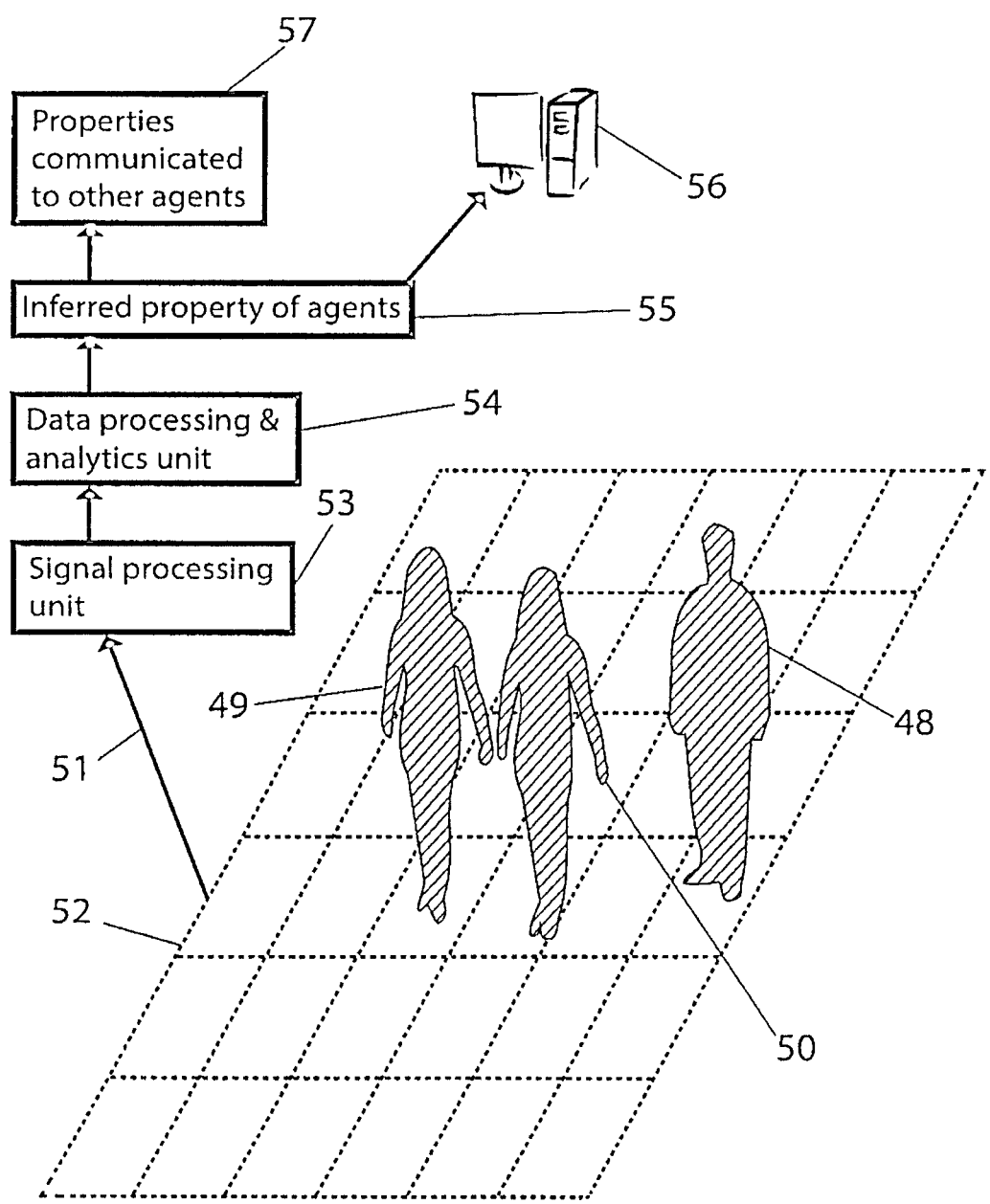
FIG. 6 shows a specific system to infer social relationships between one or more people.
Figure 7:
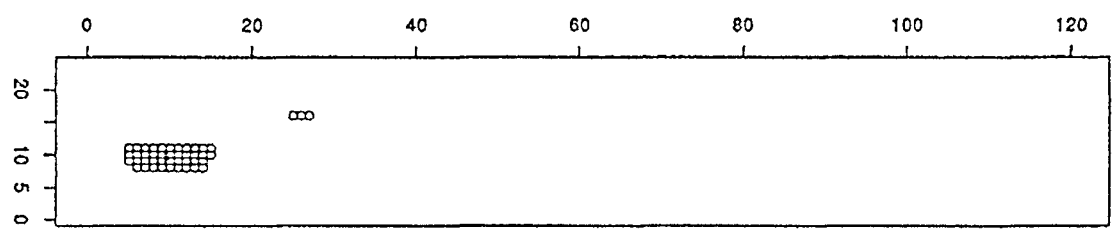
FIG. 7 shows a foot pressure data pattern where the heel of a left foot has just made contact with the sensing surface.
Figure 8:
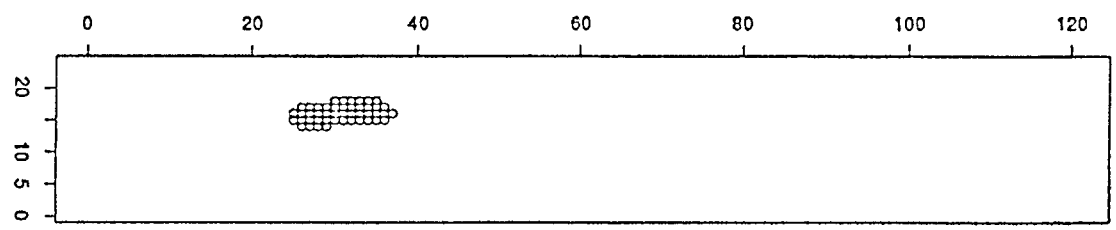
FIG. 8 shows a foot pressure data pattern where the left foot is in full contact with the sensing surface and the right foot is in the swing phase and does not have contact.
Figure 9:
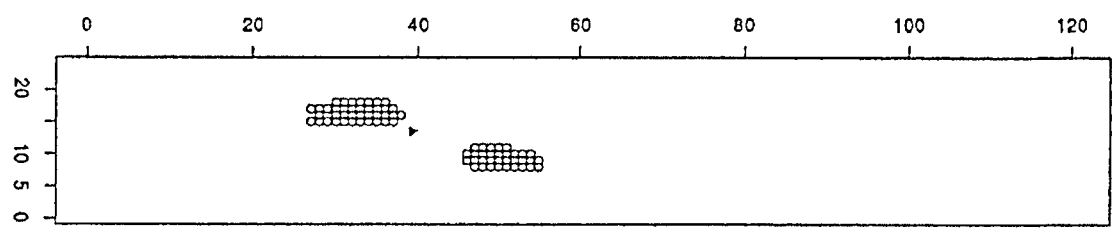
FIG. 9 shows a foot pressure data pattern where both feet are in contact while the transfer to the right foot progresses.
Figure 10:
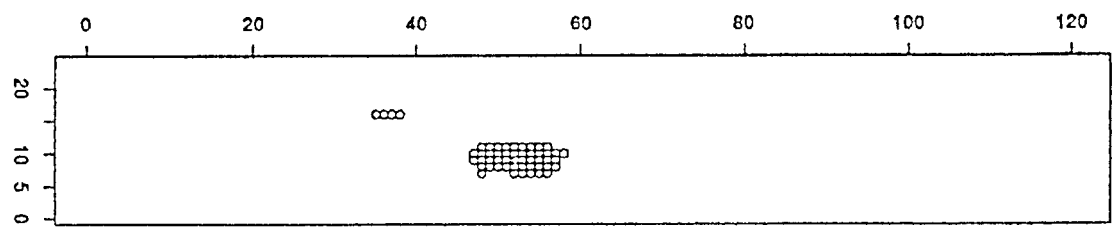
FIG. 10 shows a foot pressure data pattern where the left foot is leaving the surface.
Figure 11:
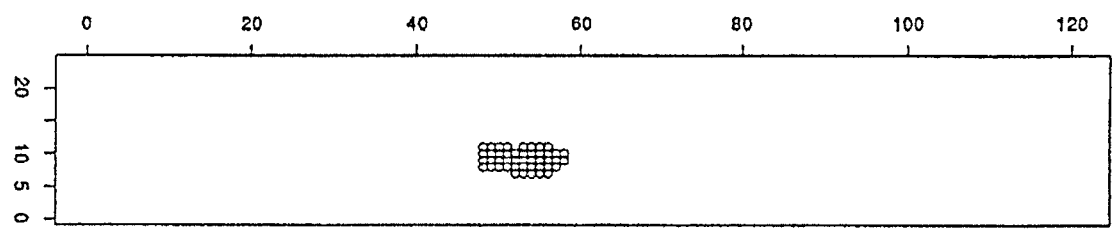
FIG. 11 shows a foot pressure data pattern where the right foot is in full contact with the surface and the left foot is in the swing phase and does not have contact.

Referring now to the drawings wherein like reference numerals refer to similar or identical parts throughout the several views, and more specifically to FIGS. 2 and 5 thereof, there is shown an apparatus 100 for determining a non-apparent attribute of an object 41. The apparatus 100 comprises a sensor portion 21 with which the object 41 makes contact and to which the object 41 applies pressure. The apparatus 100 comprises a computer 19 in communication with the sensor portion 21 that receives signals from the sensor portion 21 corresponding to the contact and pressure applied to the sensor portion 21, and determines from the signals the non-apparent attribute. The apparatus 100 comprises an output 11 in communication with the computer 19 that identifies the non-apparent attribute determined by the computer 19.

The object 41 may be a person, the non-apparent attribute may be a cognitive capacity decline, the sensor portion 21 may be a plurality of sensor tiles forming a walkway, and the signals may be indicative of gait of the person moving on the walkway.

The present invention pertains to a method for determining a non-apparent attribute of an object 41. The method comprises the steps of making contact and applying pressure with an object 41 to a sensor portion 21. There is the step of receiving signals by a computer 19 in communication with the sensor portion 21 from the sensor portion 21 corresponding to the contact and pressure applied to the sensor portion 21. There is the step of determining by the computer 19 from the signals the non-apparent attribute. There is the step of identifying at an output 11 in communication with the computer 19 the non-apparent attribute determined by the computer 19.

The object 41 may be a person, the non-apparent attribute may be a cognitive capacity decline, the sensor portion 21 may be a plurality of sensor tiles forming a walkway, and the signals may be indicative of gait of the person moving on the walkway.

The present invention pertains to a computer-implemented method to learn classifications and properties of one or more objects 41 by processing a sequence of surface contact and/or pressure measurements captured by a plurality of local contact or pressure sensing system at a time and over time. The method comprises the steps of receiving a frame or frames of the sequence which includes data for a plurality of contact or pressure measurements included in the frame. There is the step of identifying one or more collections of contact and/or pressure measurements in the frame, where each collection represents an object 41 on the surface. There is the step of generating models to extract one or more features from the contact and/or pressure measurement collections that are associated with each identified object 41. There is the step of extracting a plurality of features from the collections of contact and/or pressure measurements. There is the step of classifying each of the collections of contact and/or pressure measurements using a trained or untrained classifier. There is the step of supplying the extracted features and/or the object 41 classifications from one or more frames to a machine learning engine. There is the step of using the machine learning engine to generate values for one or more properties of one or more objects 41 and/or generate semantic representations of the behavior of one or more objects 41 over a plurality of frames, where the machine learning engine is configured to learn properties and behavior patterns observed in the contact and/or surface pressure measurements over the plurality of frames and to identify patterns of behavior by the classified objects 41.

There may be the steps of locating one or more objects 41 on the surface by detecting one or more features using a plurality of feature prediction models applied to the entire surface or to regularly or randomly selected regions of the surface, or by using similarity to an exemplar or to a reference collection of examples or to previously observed objects 41, applied to the entire surface or to regularly or randomly selected regions of the surface. There may be the steps locating and tracking one or more objects 41 on the surface by detecting their current position in a space-time window and calculating the overlap with previous detected positions or by predicting the next position of the object 41 or objects 41 using learned models from the configured machine learning engine or by applying a search algorithm using the previously detected positions.

There may be the step of reacquisition of one or more objects 41 with some level of confidence when they reenter the surface by comparing directly or with some feature transform their feature signature with stored models of objects 41 accessible by the system. There may be the step of recording the location and monitoring the paths of one or more objects 41 on the surface stored in local memory or remotely. There may be the step of the segmentation of the recorded paths of one or more objects 41 into units using learned models from the configured machine learning engine or by applying heuristic rules or rules learned from observations not based on contact or pressure data. There may be the step of the segmentation of the recorded paths of one or more objects 41 into units using measurements from other systems in real time or from stored data of the same objects 41 or exemplars of the objects 41. There may be the step of configuring of the machine learning module to infer properties of objects 41 that are correlated with contact and pressure properties of objects 41. There may be the step of identifying people from combinations of inferred properties and contact and/or pressure patterns.

There may be the step of identifying people from combinations of inferred properties and contact and/or pressure patterns and their location. There may be the step of calculating gait velocity and balance using learned models from the configured machine learning engine. There may be the step of using changes in patterns of gait velocity and balance measurements recorded at disparate times to calculate the future risk of falling using learned models from the configured machine learning engine. There may be the step of using changes in patterns of gait velocity and balance measurements recorded at disparate times and correlating them with changes in a reference collection of expert judgments about the future risk of falling based on sequences of gait velocity and balance measurements recorded at disparate times.

There may be the step of using learned models from the configured machine learning engine to predict the activity state and activity sequences of an agent. There may be the step of using observed state models and heuristically-derived state models to predict the activity state and activity sequences of an agent. There may be the steps of recording and monitoring the actions of a worker and evaluating ergonomic performance. There may be the step of providing ergonomic state and performance information to a worker, a manufacturing system, or a local or remote information system and record and store the information locally or remotely for later use or as an input to another system to make decisions, task action, or otherwise process the information. There may be the step of using learned models from the configured machine learning engine to predict the mental states of agents.

There may be the step of using learned models from the configured machine learning engine to attribute an intention to an agent. There may be the step of inferring social relationships between objects 41. There may be the step of taking actions, signaling an agent, or making decisions. There may be the step of providing information to another system as evidence to take action, signal an agent, or make decisions. There may be the step of carrying out on one or more combinations of objects 41 on the surface. There may be the step of using changes in patterns of gait velocity and balance measurements recorded at disparate times to calculate the rate of cognitive capacity decline using learned models from the configured machine learning engine.

There may be the step of using changes in patterns of gait velocity and balance measurements recorded at disparate times and correlating them with changes in a reference collection of expert judgments about the rate of cognitive capacity decline based on sequences of gait velocity and balance measurements recorded at disparate times.

In the operation of the invention, the basic embodiment of the invention consists of a system to detect a plurality of localized contact measurements with a surface, a system for collecting the measurements from one or more sensing units, and a sequence of analysis steps to make one or more representations of an object's surface contact interaction. In a preferred embodiment of the invention the system, detecting localized contact with a surface, consists of a plurality of pressure sensing elements in an array on a surface and a system for collecting the measurements from each of the pressure-sensing units. The contact sensing surface may cover a floor in part or in whole or is integrated with or lays under a floor, but the localized contact detection system or pressure sensing elements might be deployed to cover or be integrated into or placed under, in part or in whole, various surfaces. Such surfaces include, but are not limited to, walls, tables, furniture, decks in vehicles and ships, uneven or multilevel floors, sports and training surfaces, roads, or land forms. The sensing units may be integrated into a pressure sensing surface or otherwise cover, be integrated with, or be beneath regions of the surface. A specific embodiment of the invention uses pressure sensing arrays such as the mechanically interpolating pressure sensing tiles provided by Tactonic Technologies LLC.

The localized contact detection system or pressure sensing surface may be deployed on a permanent, semi-permanent or temporary basis and may not necessarily be restricted by environment. For example the surface can be in a doctor's office or a clinic, indoors or outdoors, in a public or private space, or in a factory or a residence, or integrated with a road or other paved surface.

The employed sensing system can monitor substantially all of the surface or just a limited portion thereof. The portion monitored can be contiguous or as separated patches or a collection of points. As the object, such as person or agent, makes contact or moves on the surface, signals are generated by one or more of the sensor units. These signals are collected by electronic systems and converted to a digital signal. Such a digital representation is convenient for the data processing steps, but it can be seen that a digital signal is not required for the processing steps, as any mathematical representation of the array of contact or pressure signals is sufficient as an input to the processing.

In one specific embodiment, a one or more pressure sensing tiles, each with a plurality of pressure sensing units or elements, may be deployed to cover a run in a residential hallway. Selection of a location might be made to have cases where a person can be expected to walk a number of times during the day, or in a location where routine or expected behaviors might be inferred, for example use of a bathroom or entry/exit from a bedroom. In this way, in addition to the direct pressure measurement of the agent/person, the timing and frequency of observations may also provide information for extraction of features or inferring the behavior, intent, or changes in personal habits of the agent/person. In a general way such types of context information can be understood to be of use for analysis and interpretation of contact and/or pressure measurement data in various concrete embodiments of the system. The descriptions of the analysis used in the invention should be understood to be extended to use such information appropriately, both as features to learn models and as inputs to models used for calculation, and in rules relating to the creation and use of models and inferences. Such uses of the models and inferences by the invention can include communication with humans or other systems and decisions to apply application programs or systems.

After collecting information from the sensor elements over any finite unit of time, the electronic processing unit for the contact or pressure sensing tiles will record the data. That data can be stored for off-line analysis or streamed to a system for continuous analysis.

In the descriptions of invention embodiments, it is to be understood that object, agent, and human or person are to be used interchangeably where it is reasonable to do so. For example, general feature extraction can relate to any property of an object, including agents and humans. On the other hand, when attributing intent or mental states it is to be understood that only objects capable of having such properties are intended as the referents. References to objects, agents, persons and human are not intended to be limiting in any way in the following and do not exclude animals, mechanical devices or systems, or composites of objects. For example, it is to be understood that the inference of a behavior or intent for a controlled vehicle is within the scope of the invention.

Figure 1:
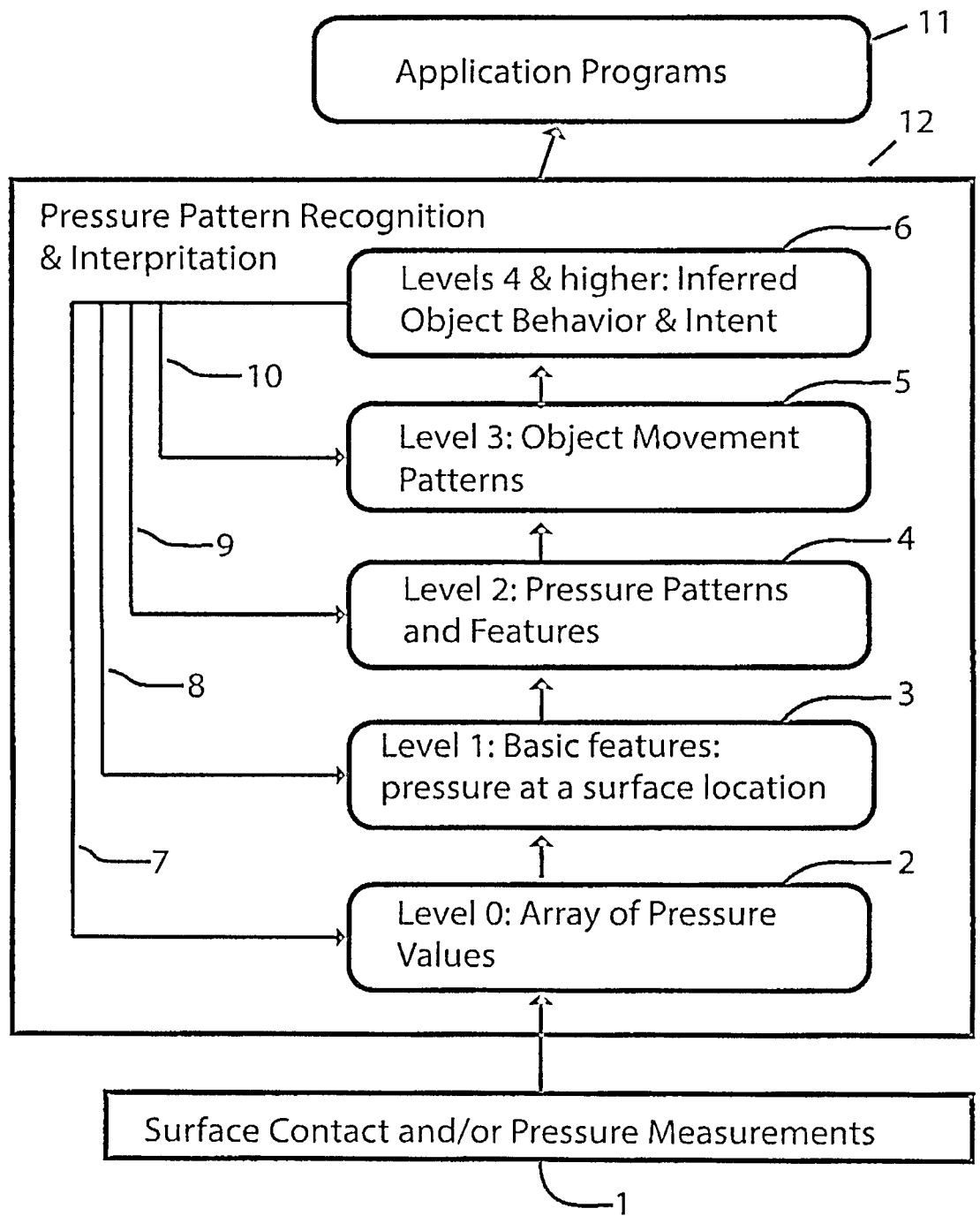
FIG. 1 shows the several levels of acquiring and processing the surface data observations.

FIG. 1 provides a general sketch and illustration of the data processing levels in the invention. It can be seen that the pressure pattern recognition and interpretation system 12 consists of multiple processing levels that provide progressively higher-level or more abstract representations of objects on a surface. The operations illustrated in FIG. 1 generally consist of accepting a set of data inputs 1 directly from the contact and/or pressure sensing system or from a system that stores the data from the contact and/or pressure sensing system. The input data can be processed as complete frames covering an area or time segment, or as samples of the input data, for example as a collection of regions on the surface or a time segment sample of the sensor data or a data sample based on some other dimension. At LEVEL 0 an array of pressure data values 2, which can be pressure measurements or local contact indications categorically encoded to correspond to 'contact' or 'no contact', is created from the input. LEVEL 1 processes the LEVEL 0 information to determine basic features of the observations 3 and makes a pressure or contact representation. LEVEL 2 analyses the contact and/or pressure representation to extract patterns and features of the representation 4. Such features can include object recognition and object properties. LEVEL 3 processes the LEVEL 2 results to learn object movement patterns 5. LEVEL 4 and above infers object movement behavior and intent 6. The objects and their behavior are analyzed using a variety of statistical modeling techniques applied to the input data and to representation results derived from one or more layers of processing. It is to be understood that the results from one level can be used to enrich or improve the results derived at another level, as indicated for example by 8. This derivation and use of results from any particular level is to be understood as applying in a general way and the results of processing at any level provides features and interpretation rules that can provide inputs or decision criteria useful for processing at any other layer or a plurality of layers and may be combined without limitation. For example 7 might indicate a classification model derived at LEVEL 3 5 being used to impute missing data in LEVEL 0 2. Generally, the results of the pressure pattern recognition and interpretation system 12 can be made available to one or more application programs 11. It is to be understood that the results can consist of results from one level of processing or of any mixture of levels of processing and they can be individually and collectively used as inputs to application programs in local or remote systems that achieve particular utility. For example, applications that present predictions of the probability of a person falling in some forecast time period, identification of authorized or unauthorized persons or objects in a security zone, taking notice of or acting on anomalous object or agent behaviors, or predicting properties of people, such as their state of attention or decision making, or social relationships with other people. The results can be stored locally or remotely for analysis or later use. Further, the results and/or interpretation of the results of the invention processing can be communicated to a human or some other system, or can be used in a decision-making process that might invoke an action, including selection and execution of an application program or communication with some system. Particular embodiments of the invention provide details of the processing at various levels, especially as they relate to achieving objects of the invention and providing specific utility.

Another aspect of the embodiment of the invention has a computer-implemented system as illustrated in FIG. 2 which includes a system having the contact and/or pressure sensing input source 21 configured to provide a sequence of contact and/or pressure image frames, each depicting the contact and/or pressure measurements on the surface at a time, a processor 14, which may include a hardware processor 14, and memory 18, which may include a non-transitory storage medium, containing modules and programs to process the input contact and/or pressure data 16, 18. When executed on the processor the contact and/or pressure data processing module program 16 provides a suitable representation of the data that can be output 13 or used as an input to the modeling module 17. When executed on the processor the machine learning program 17 performs operations that analyze the contact and/or pressure measurements at a time and over a sequence of such pressure image frames to carry out one or more of the steps in FIG. 1.

In the preferred embodiment, one or multiple objects on the surface are located by processing the input data or by sampling the input data to find positive contact and/or pressure measurements. The input data may be sampled using a regular sampling pattern or a random sampling procedure, with or without constraints. When a positive result is detected nearby sensor outputs are processed to learn the boundaries and contact and/or pressure profile of the object.

One embodiment of the invention uses one or more Hough filters or Hough forests from one or more of the processing levels trained using labeled input data to assign a probability that a specific type of object or an object in a particular state or with certain properties is at a location on the surface based on the contact and/or pressure profile and other properties of the data. Any object detection algorithm could be used however, for example detection using density clustering, and those trained in the art recognize that many supervised and unsupervised machine learning techniques and signal processing techniques can be used to determine the positions and contact shapes of the objects on the surface with some level of confidence. A specific object detection process using Hough forests employs the well-known Hough transform and the random forest technique, an ensemble of random decision trees. Hough forests allow fast application to input data and are also efficiently trained, and are suitable for interactive applications as well as invention embodiments that cover large surfaces with many objects on the surface. A Hough forest can be trained using example contact and pressure data. For each object a bounding area is identified and the area is associated with the object class and the properties of the object. For example, an object class might be 'human' and a list of properties could include 'female', 'age between 20 and 30', 'walking with friend', 'wearing sneakers' and so on. There is no limitation on the number or type of properties and they can include relatively stable physical properties, transient physical properties including motions, and non-physical properties such as intentional states. The selection of an object bounding area and the associations of class and properties can be performed manually or using some automated technique, including the application of algorithms to find similar examples in databases or in reference systems. For each object, the contact and pressure measurements in the bounding area are associated with a vector noting the absence or presence of each of the properties that are used to detect the objects. The collection of such training examples is then input to a random forest algorithm to make a classification model that is used for detection. It is typical that a collection of models are created, each for the detection of a single feature. In such cases, the training sets note only the presence or absence of the property for the classification model. The detection of an object proceeds by inputting measurements in a region of the surface that can be selected randomly, or sampled using some procedure, and then applying the collection of detection model which vote whether the object or property they detect is present. Such a vote can be categorical or not depending on whether a classification model or a regression model was used. It can be seen that by successive sampling of the surface, objects and properties of objects can be detected with some confidence level.

Once an object has been located with sufficient confidence, the invention continues to monitor and sample the region as appropriate to confirm the existence and properties of the object and to alter the region to track the positive contact and/or pressure sensor outputs as the object moves, either by predicting the expected possible locations of the object or by using a search algorithm. Such object locations, both identified and predicted, and object properties can be used immediately or stored and updated in a database or via some other persistence mechanism directly or remotely accessible by a processor. The collection of inferred object properties can be used as an object identifier and used to reacquire the object if it leaves the sensing surface and later returns or enters a different sensing surface. Such reacquisition could take place even at long time scales but with lower confidence based on uncertainties associated with one or more features of the object, for example if a person's weight has changed significantly. The object properties can be related in a model of the object and inferences about the object identity, or distinguishing the object from other objects, can be achieved by suitable calculations on the model as will be appreciated by those trained in the art. For example, a woman might be identified with a collection of features when entering a store, where she purchases a pair of shoes and changes her shoes. Upon re-entry to the sensing surface the system can apply functional transforms to the model that correspond to changes in pressure distribution and gait profile for different shoe types. A simpler example is the case where the person picks up another object and thus increases their weight. In such cases, the invention can make an identification prediction with some level of confidence, even when there are temporal gaps in the observations of the object. Such relationships between model features and other properties of the model can be learned empirically from observations using various modeling techniques or calculated using a suitable causal or probabilistic model of the system that imposes such changes on the object or be applied from heuristic rules or learned from association rule mining on observations of the objects, including image-based or other sensing techniques, or from other data sets.

A specific example of application of the preferred invention embodiment, the input data can be analyzed to find footsteps and extract measurements of footstep properties and the gait of the person. Use of walkers, canes and other supportive devices can be identified and distinguished by their relatively consistent shapes and/or pressure patterns along with a path trace that coheres with the paths of the footsteps, for example one expects the path of the support device contact points to be roughly parallel to those of the footsteps.

One process by which footsteps can be detected is to identify the boundaries of the locations that have positive contact and/or pressure measurements using density-based clustering or combining density-based clustering with a cluster-center and a distance matrix to identify contact clusters that likely belong to the same foot. The assertion that one or more contact clusters are part of the same foot can be confirmed by successful prediction of expected locations and pressure and/or contact features, including shape and pressure distributions. This procedure can be generalized to associate identified contact and pressure areas with a single object having several areas of contact with the surface. Other unsupervised, semi-supervised or supervised machine learning techniques can be used to identify the local contact and/or pressure regions. In multi-object cases, coherent patterns of such measurements will indicate at some confidence level the presence of a person or object at a location. For example, coherent locomotion patterns of two feet in a walking gait or some other gait can be identified and distinguished. Likewise, the locomotion of a wheeled vehicle or other object can be identified by comparison to known patterns of contact and pressure characteristics of moving objects. Such coherent locomotion contact and/or pressure patterns can also be learned using various machine learning techniques, for example by using a hidden Markov model or a convolutional neural network.

When the feet are identified from sensor data for the region holding a footstep is collected and the location and properties of the pressure data in the region can be calculated. One such calculation is the center of the pressure measurements.

Gait parameters are calculated from the timing and location of subsequent footsteps. The calculated gait parameters include instantaneous and average gait velocity, the swing time of a footstep, stride length, pronation and supination, duration of distinct foot contact phases and differences of the foot parameters, including event times and locations, from footstep to footstep and stride to stride. The invention records, classifies, and compares patterns of gait parameters over time periods. Changes in these patterns are classified using a trained classifier to measure current values of properties of a person and predict future values, such as the likelihood of falling.

An embodiment of the invention infers a person's balance from the moment-to-moment variations in the center of pressure within a footstep and over multiple footsteps. One specific technique is to calculate the standard deviation of the center of pressure resolved into medial-lateral and anterior-posterior components relative to the foot orientation. Other formulas can be applied to make such measurements of balance.

For all object properties and features, patterns of statistical properties and sequences of the pressure observations can be recorded and stored. Changes in such pattern properties over time can be used as inputs to calculate historical trends and make predictions about the future value of properties and features of an object. One example is prediction of the expected gait velocity and balance of a person. A specific utility of such predictive capacity of the invention is the calculation of the future probability of falling, which has been correlated with declines in observed gait velocity and deteriorating balance. In addition, the pattern of changes produced by the invention provide inputs to a classifier trained using expert human judgment of the future risk of falling to make predictions that supplement or replace such expert judgments. These human judgments of the future risk of falling can be based on clinical tests to assess fall risk potential, such as but not limited to a test measuring the time needed for a person to rise from a seated position and begin walking (Timed Up and Go or TUG), or observing the ability of the person to maintain their stance when disturbed by a light push. Another specific utility of the predictive capacity of the invention as applied to gait analysis and the pattern of gait property changes is the prediction of cognitive decline from gait velocity and other gait properties as compared to a history of measurements. In the same way the pattern of changes provide inputs to a classifier trained using expert human judgment of future cognitive capacity to make predictions that supplement or replace such expert judgments. These human judgments of cognitive decline can be based on clinical tests including the TUG test amongst others.

The contact and/or pressure data, and any or all of the analytical representations of the data, for example identification of footsteps, locomotion path segments, or inferred states of an agent, can be transmitted in various ways, including digitally, to a remote location for further analysis, distribution, or to provide evidence for a decision and/or action by humans or a computer-implemented system. Additionally, the data and any analytical representations of the data can be used at the site where it was collected to provide evidence for a decision and/or action by humans or a computer-implemented system.

Figure 3:
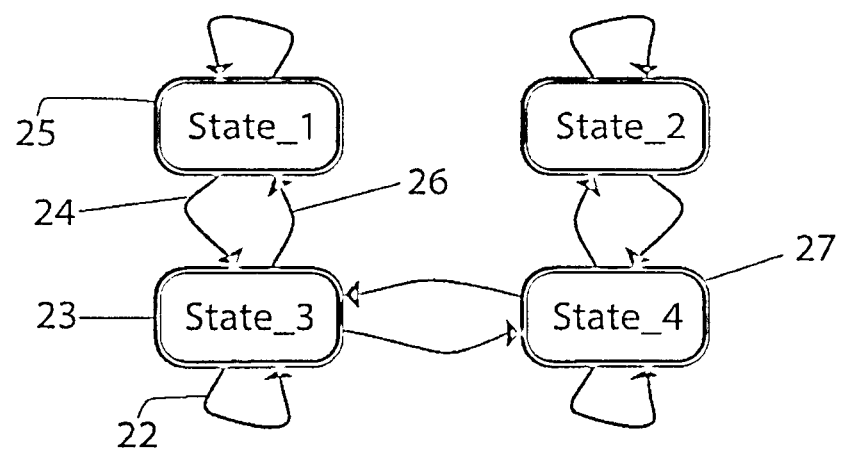
FIG. 3 shows an example Markov state model of an object.

Object behaviors can be learned by applying techniques to first identify the locomotion paths of an object and then segmenting the path using a trained classifier. Object paths may also be segmented using heuristic rules or rules learned from other types of data, for example visual observations of object movements and/or object movement patterns. The path segments and the dynamic and persistent features of the objects during each path segment are input to a trained classified whose output is a behavior label for the object. A specific embodiment uses locomotion traces and the associated pressure- and non-pressure-based features to train a Markov model of human movement. FIG. 3 illustrates an example of a generic Markov state model. Each state, for example, STATE_4 27, is associated with a pose, for example standing upright in place. STATE_3 23 could be the state of walking in a relatively straight line and STATE_1 25 could be the state of running. The transition from walking to running is indicated by 24. For each time unit a person is in one of the activity states. 22 indicates the person continued walking in the unit time. It is apparent that this simple model can be extended appropriately to cover an arbitrary number of action states. The structure of such models can be made from human knowledge and heuristics and the states and transitions can have a known interpretation, however the states and transitions can also be learned directly from the data using various techniques that can provide classifications of contact and/or pressure data that correspond to action states and identification of state transitions, including clustering, neural networks, decision tree ensembles, and multilevel classification approaches using one or many types of models. In the invention the indicative contact and/or pressure patterns for states are learned from observations of objects in that activity state, or inferred from contact and/or pressure pattern models of other activity states, either singly or in combinations. A training collection of behaviors is produced by using sequences of actions in a locomotion sequence and then manually assigning the action sequence to a behavior, or applying some algorithm such as similarity to a reference collection of behaviors or previously observed action sequences. This training collection provides an input to a support vector machine to make a behavior prediction model. The invention inputs a locomotion sequence of actions and object properties to the prediction model and assigns a behavior to the object for the segment. It is apparent that sequences of behaviors can be used in training sets to make predictive models that accept sequences of behaviors to predict object behaviors as well. Intentions can be assigned to objects based on the behaviors by using classifiers trained with data sets where intentions have been assigned to behaviors and collections of behaviors manually or algorithmically from similarity to associations of intention to behaviors in reference data sets or by similarity to observed behaviors to which intentions have been associated. Support vector machines are used in a specific embodiment of this aspect of the invention, but it is apparent that other supervised machine learning techniques can be used as well. A variant of this embodiment of the invention uses k-mean clustering to learn groupings of action sequence patterns in the locomotion segments to make assignments of behaviors without attributing interpretable class labels. In the same way such unsupervised techniques are used to attribute a distinct class of intention to a locomotion sequence without interpretation. It is apparent that such systems can be dynamically extended to distinguish new types of behaviors and intentions from the input data.

In a specific embodiment of the invention, a number of pressure sensing tiles, each with a number of pressure sensing units or elements, are deployed to cover a work area, for example a station or zone on an assembly line. The pressure data of a worker is recorded and the pressure data is analyzed using the activity state model to identify the activity states and state transitions to characterize their work activities as a sequence of poses and actions, for example actions to assemble a product. The analysis includes counts of assumed poses, including the number of poses of specific types, for example ones that have certain profiles of balance that indicate stretching or awkward stances, the number of steps and other movements, and various statistical and other calculations on their actions and action sequences. One utility of such an invention embodiment is to provide objective data to support ergonomic evaluation of a worker's actions and work environment. The recorded work activity and pose information can be recorded for later analysis, transmitted for remote processing and analysis and/or processed locally. The resulting analysis can be used to provide feedback to the worker to reduce ergonomic risks, such as work-related musculoskeletal disorders, by altering their activity. The analysis can be used to modify the work environment by adjusting tools, production processes or environmental conditions.

In one embodiment a Markov model of human, agent, or object movement is applied to new object trace instances to identify changes in locomotion state, for example stopping or turning, to segment the object locomotion trace. A model is trained using observed segment data that has been labeled with human judgments of behavior and intent. Observed locomotion segments can then be classified and behaviors and intents assigned to the person or object. In another embodiment the model is trained using unordered locomotion segment sequences to allow observed locomotion data to be distinguished as probably belonging to one or more behavior or intent classes. Another specific embodiment is to use a convolutional neural network to learn the actions and/or action sequence segments from the input data. Yet another specific embodiment is to use random forest decision tree ensembles to learn the actions and/or action sequence segments. Such distinguished locomotion properties can be interpreted to some degree by humans or systems using contextual or other information that is exogenous to the locomotion traces. For example, a person whose locomotion behavior class is characterized by relatively straight line and constant motion that is not aligned with an entrance to a store can be interpreted as a probable instance of 'not browsing' behavior. This label can be applied to the locomotion behavior class and used in the training of an improved behavior prediction model. In this way the predictive performance of the invention can be incrementally improved and the domain of utility can be extended.

In another embodiment, sequences of segments are used to train the behavior classification model or as inputs to an unsupervised classification model. Further, the behavior and intent modeling can also use with input locomotion segments that have been enhanced with other features of the person, agent, or object, for example statistics of gait parameters or activity state changes during the segment. Additionally, the contextual features of location or environmental or other conditions exogenous to the contact and/or pressure measurements can be used. Such models can be used individually or in combinations to predict and assign labels to an input to the system that embodies the invention. Such models can also be used to modify the inputs provided to classification models, both in the process of creating new models and in operational settings to make calculations using established models. Various machine learning approaches can be used to make such models including decision trees, random forests, hidden Markov models, and neural networks, including convolutional neural networks. Reinforcement learning can be used with segments and segment sequences by assigning locomotion and activity goals and an associated utility function. Unsupervised machine learning approaches can also be used, including clustering, association rule mining, self-organizing maps, and dimensionality reduction techniques, such as Principle Component Analysis, to distinguish behaviors.

The invention can identify anomalous behaviors by determining if an observed segment pattern is a member of a previously learned behavior class. One particular technique to identify anomalous behaviors using contact and/or pressure input data that has been processed to identify object paths is to use a multi-layer process of clustering and sequencing as taught in U.S. Pat. No. 8,494,222 for visual observations of object paths. An anomalous behavior is detected when the observed pattern does not have an acceptable fit with one or more of a collection of behavior patterns as determined by application of rules learned using association rule mining techniques or by application of Markov Logic Networks or rules set heuristically. The invention can also detect anomalous behaviors by calculating the similarity of the observed behavior patterns to stored or calculated parameters of known behavior patterns or by exchangeability with generated sequences of known patterns, as produced, for example, using a generative process implemented by the system, for example by using urn processes. The degree of similarity or exchangeability to infer anomalous or normal or expected behavior can be set heuristically or by learning from training examples using supervised or semi-supervised techniques or learned directly with unsupervised techniques. In comparing the observed behavior with the reference rules and pattern classes, it is to be understood that the reference rules and pattern classes can include positive and negative behavior class instances with respect to normal, expected, or anomalous behavior patterns and the interpretation of the results of comparing the observed behavior pattern is appropriately adjusted. For example, an observed pattern that is measured as significantly similar to a pattern or patterns that have been labeled as anomalous or suspicious will be interpreted as anomalous behavior as would an observed behavior pattern that fit none of the behavior patterns accessible by the system. The system can generate an alert signal to a human or another system when an anomalous behavior is detected or the system can communicate with another system to record the behavior and/or provide an input to monitor or make a decision, for example to take some automated action.

Figure 4:
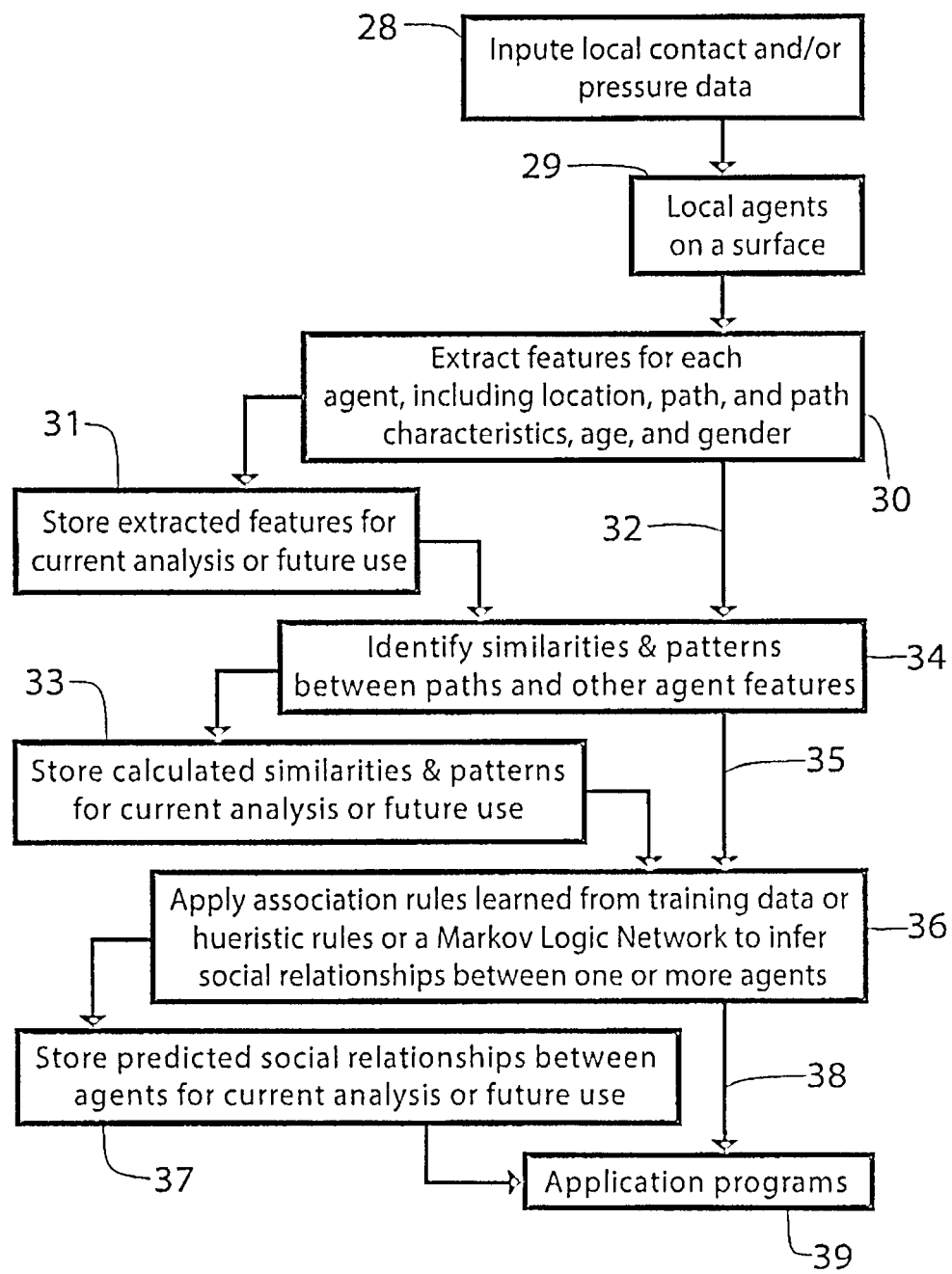
FIG. 4 shows a method of processing surface data observations to infer social relationships between agents on the surface.

The invention is able to infer social relationships between people on a surface using a technique similar to that taught for processing a series of visual images by U.S. Pat. No. 7,953,690. FIG. 4 illustrates a process by which social relationships can be inferred in an embodiment of the present invention from surface contact and/or pressure data 28. The process first locates people or agents on a surface 29 using techniques disclosed above, and then extracts features for each agent, including location, path and path characteristics, and other features including probable age range and gender 30. The extracted features can be stored locally or remotely for analysis or future use 31. The features and the locomotion paths for the collection of agents can then be analyzed using various techniques, including calculation of similarities and relationships between patterns thereof 34. Such similarities and patterns may include calculation of the degree of exchangeability between paths and subsequences of paths. Such calculations and analysis can be carried out on pairs or agents or on any combination of agents and the results can be stored for current analysis or future use 33. Association rules learned from training data or heuristic rules or a Markov Logic Network are then applied to the identified similarities and patterns between two or more agents to infer social relationships 36. The inferred social relationships can be stored for additional analysis or future use 37, or they can be provided to one or more application programs 39 or communicated to humans or other systems or used to decide to trigger some action, for example fashioning and/or communicating a commercial offer to people with an inferred social relationship. In the foregoing, it is to be understood that the invention can infer social relationships not only for individuals, but also for and between groups of individuals with suitable rules and application of the similarity and pattern comparison algorithms. For example, relationships between teams of agents can be inferred using the same techniques.

It can be seen that the objects of the invention set forth in the preceding description, are efficiently attained and that certain changes can made in carrying out the above method and construction(s) without departing from the spirit and scope of the invention. Those trained in the art of machine learning will recognize that a variety of supervised, semi-supervised and unsupervised modeling techniques can be used alone or in combinations to process the data inputs, perform the higher level analysis, and to create and apply models to accomplish the various invention utilities. It is intended that all matter contained in the above description and shown in the accompanying drawings shall be interpreted as illustrative and not in a limiting sense.

REFERENCES CITED (ALL OF WHICH ARE INCORPORATED BY REFERENCE HEREIN)

| U.S. PATENT DOCUMENTS | | |
|---|---|---|
| 8,138,882 | | |
| A * March 2012 Mai Do, et al. | | 340/5.1 |
| 8,494,222 | | |
| B2 * July 2013 Cobb, et al. | | 382/305,312 |
| 7,953,690 | | |
| May 2011 Luo, et al. | | 706/47 |
| 5,952,585 | | |
| June 1997 Trantzas and Haas | | 338/47 |
| EP PATENT APPLICATION DOCUMENTS | | |
| EP20,130,177,483 | | |
| January 2014 Greene | | |

OTHER PUBLICATIONS

[1] Anne F Ambrose, Mohan L Noone, V G Pradeep, Beena Johnson, K A Salam, and Joe Verghese. Gait and cognition in older adults: Insights from the Bronx and Kerala. Ann Indian Acad Neurol, 13(Suppl 2):S99-S103, December 2010.

[2] D. Austin, T. Leen, T. L. Hayes, J. Kaye, H. Jimison, N. Mattek, and M. Pavel. Model-based inference of cognitive processes from unobtrusive gait velocity Measurements. In Engineering in Medicine and Biology Society (EMBC), 2010 Annual International Conference of the IEEE, pages 5230-5233, August 2010.

[3] Moez Baccouche, Franck Mamalet, Christian Wolf, Christophe Garcia, and Atilla Baskurt. Sequential Deep Learning for Human Action Recognition. In Proceedings of the Second International Conference on Human Behavior Unterstanding, HBU'11, pages 29-39, Berlin, Heidelberg, 2011. Springer-Verlag.

[4] Alan Branzel, Christian Holtz, Daniel Hoffmann, Dominik Schmidt, Marius Knaust, Patrick Luhne, Rene Meusel, Stephan Richter, and Patrick Baudisch. GravitySpace: Tracking Users and Their Poses in a Smart Room Using a 2D Pressure-Sensing Floor. In CHI 2013. ACM, 2013.

[5] Takuya Murakita, Tetsushi Ikeda, and Hiroshi Ishiguro. Human Tracking using Floor Sensors based on the Markov Chain Monte Carlo Method. In ICPR (4), pages 917-920, 2004.

[6] R. J. Orr and G. D. Abowd. The Smart Floor: A Mechanism for Natural User Identification and Tracking. In Conference on Human Factors in Computing Systems, pages 275-276, 2000.

[7] Gang Qian, Jiqing Zhang, and Assegid Kidané. People Identification Using Gait Via Floor Pressure Sensing and Analysis. In Proceedings of the 3rd European Conference on Smart Sensing and Context, EuroSSC '08, pages 83-98, Berlin, Heidelberg, 2008. Springer-Verlag.

[8] Ruben Vera Rodriguez, Richard P. Lewis, John S. D. Mason, and Nicholas W. D. Evans. Footstep Recognition for a Smart Home Environment. International Journal of Smart Home, 2(2):95-110, April 2002.

[9] Axel Steinhage and Christi Lauterbach. Monitoring Movement Behavior by Means of a Large Area Proximity Sensor Array in the Floor. In Bjorn Gottfried and Hamid K. Aghajan, editors, BMI, volume 396 of CEUR Workshop Proceedings, pages 15-27. CEUR-WS.org, 2008.

[10] Miika Valtonen, Jaakko Maentausta, and Jukka Vanhala. TileTrack: Capacitive Human Tracking using Floor Tiles. In PerCom, pages 1-10. IEEE Computer Society, 2009.

[11] F. Wang, E. Stone, M. Skubic, J. M. Keller, C. Abbott, and M. Rantz. Toward a Passive Low-Cost In-Home Gait Assessment System for Older Adults. Biomedical and Health Informatics, IEEE Journal of, 17(2):346-355, 2013.

[12] William H. Warren and Brett R. Fajen. Behavioral Dynamics of Visually-Guided Locomotion. In A. Fuchs and V. Jirsa, editors, Coordination: Neural, behavioral, and social dynamics. Springer, Heidelberg, 2008.

It is also to be understood that the following claims are intended to cover all of the generic and specific features of the invention herein described and all statements of the scope of the invention which, as a matter of language, might be said to fall there between.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. An apparatus for determining a non-apparent attribute of a person comprising:

a sensor portion of a plurality of sensor tiles forming a walkway with which the person makes contact and to which the person applies pressure a number of times a day; and a computer in communication with the sensor portion that receives signals indicative of gait of the person moving on the walkway the number of times a day from the sensor portion corresponding to the contact and pressure applied to the sensor portion by the person, determines from the signals over time the non-apparent attribute based on center of pressure measurements of footsteps of the person.

2. A method for determining a non-apparent attribute of a person comprising the steps of:

making contact and applying pressure with a person to a sensor portion of a plurality of sensor tiles forming a walkway a number of times a day;

receiving signals by a computer in communication with the sensor portion from the sensor portion corresponding to the contact and pressure applied to the sensor portion indicative of gait of the person moving on the walkway the number of times a day;

determining by the computer from the signals the non-apparent attribute based on center of pressure measurements of footsteps of the person; and identifying at an output in communication with the computer the non-apparent attribute determined by the computer.

3. A system to detect a plurality of localized pressure contact measurements with a surface comprising:

one or more stationary sensing units for collecting the pressure contact measurements; and a computer in communication with the sensing units which makes one or more representations of an object's surface pressure contact interaction and extracts patterns and features of the representations to infer object movement behavior and intent utilizing a program stored in a memory of the computer having multiple processing levels that provide progressively higher level representations of the object from the pressure contact measurements.

\* \* \* \* \*